United States Patent [19]

Butts

[11] Patent Number: Plant 6,975

[45] Date of Patent: Aug. 8, 1989

[54] PLUM TREE, "MAJESTIC M"

[76] Inventor: Merle R. Butts, 6770 S. Reed Ave., Reedley, Calif. 93654

[21] Appl. No.: 202,599

[22] Filed: Jun. 6, 1988

[51] Int. Cl.[4] ..... A01H 5/00

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of Plum Tree which is characterized as to novelty by a date of maturity for harvest and shipment during the second or third week of October under the ecological conditions prevailing near Orosi, Calif.; the date of harvesting being approximately two or three weeks later than the Angeleno Plum Tree (U.S. Plant Pat. No. 2,747) with which it is most closely similar in its overall physical characteristics, and approximately ten weeks later than the Friar Plum Tree from which it was discovered as a chance sport, and which is further distinguished as to novelty by producing uniformly shaped fruit which have exceptional storage and shipping characteristics.

1 Drawing Sheet

BACKGROUND OF THE NEW VARIETY

The present invention relates to a new and distinct variety of Plum Tree, denominated varietally as "Majestic M" and more particularly to such a plum tree which bears a full freestone fruit which has a flesh which has a crisp texture and a yellowish-brown color and which is principally characterized as to novelty by a date of ripening of approximately October 15 through October 20, in the San Joaquin Valley of Central California.

From an economic standpoint, the relative dates of ripening of various varieties of plums is obviously of extreme importance. It has long been recognized as desirable to provide a plum tree that bears fruit later in the season than other varieties of plum trees which it most nearly resembles whereby the fruit can be sent to market at a time when competition is at a minimum. In addition, if the harvesting periods of various plums can be effectively spread over a longer period of time, considerable savings and increased efficiency can be attained because the capitol expenditures required to harvest and transport such plums can be spread over a longer period of time resulting in lower costs of the final product and increasing uniformity and production.

The new and distinct variety of Plum Tree, "Majestic M" is further characterized as to novelty by producing fruit which are somewhat remotely similar in their physical characteristics to the plum produced by the Angeleno Plum Tree, U.S. Plant Pat. No. 2,747, said Angeleno Plum Tree maturing for harvesting and shipment in middle or later September in the San Joaquin Valley of Central California and in addition by producing fruit which have noteworthy storage and handling characteristics.

ORIGIN AND ASEXUAL REPRODUCTION OF THE NEW VARIETY

The new and distinct variety of Plum Tree hereof was discovered by the Applicant, as a chance sport, during routine orchard operations in 1984. The sport, which was discovered in the cultivated area of an orchard owned by the Applicant and which is located between Road 164 and Avenue 416, approximately five miles east of Orosi, Calif., in the County of Tulare, was found growing on what is believed to be a Friar Plum Tree (believed unpatented), the tree of origin having been damaged on an earlier occasion by mechanical harvesting equipment. Upon discovering the chance sport the inventor marked the tree and thereafter continuously observed it for purposes of determining its characteristics. It was subsequently determined that the sport produced fruit which matured for harvesting and shipment at a date noticeably later than that of the surrounding Friar Plum Trees, which are ripe for commercial harvesting and shipment approximately the end of July in the San Joaquin Valley of Central California. The Applicant subsequently removed wood from the chance sport, and grafted it into Nemaguard rootstock for purposes of further evaluation. This first asexual reproduction occurred in the Fall of 1984. A first evaluation of the fruit produced by the chance sport was accomplished in 1984. It was during this first evaluation that the Applicant discovered, upon a comparison of the subject plant with other known varieties of plum trees, that the instant variety "Majestic M" was indeed a new and distinct variety of plum tree. The Applicant has continually observed the subject variety and it has been determined that the asexually reproduced progeny exhibit the same distinctive characteristics as the original sport.

The "Majestic M" Plum Tree of the present invention is noteworthy in ripening approximately ten weeks later than the Friar Plum Tree (believed unpatented), and from which it was derived as a chance sport, and approximately two or three weeks later than the Angeleno Plum Tree (U.S. Plant Pat. No. 2,747) with which it is most closely similar with respect to its physical characteristics, but which is distinguished therefrom by producing fruit which have a greatly improved fruit quality and which further have a good flavor and have a crisp and juicy fruit texture.

BRIEF DESCRIPTION OF THE DRAWINGS

The accompanying drawing is a color photograph of three mature fruit of the subject variety, two of which display their external coloration sufficiently mature for harvesting and shipment, and one of which has been divided in the axial plane to display the flesh and stone coloration, together with a pair of leaves which display the coloration of their upper and lower surfaces and a representative sample of bark all of the subject variety.

DETAILED DESCRIPTION

Referring more specifically to the pomological details of this new and distinct variety of Plum Tree, the following has been observed under the ecological conditions prevailing at the Applicant's orchard which is located near Orosi, Calif. All major color code plate identifications are by reference to the Dictionary of Color by Maerz and Paul, Second Edition, published in 1950 or alternatively by reference to the Inter-Society Color Council - National Bureau of Standards Centroid Color Charts. Common color names are also employed occasionally.

TREE

Size:
- *Generally.*—Average.

Productivity: Productive.

Figure: Semi-spreading, depending upon pruning practices.

Regularity of bearing: Regular.

Trunk:
- *Length.*—Generally — average.
- *Surface texture.*—Rough; the bark of the subject variety is not particularly noteworthy.

Branches:
- *Size.*—Generally — Stocky.
- *Surface texture.*—Average.
- *Color.*—A dark olive-green, Plate 24, E-6, Page 71; (127 gy. O1 G).
- *Lenticels — numbers.*—Numerous.
- *Lenticels — size.*—Variable, approximately 5 through 7 mm.

LEAVES

Size:
- *Generally.*—Medium.
- *Average length.*—Approximately 92 through 97 mm.
- *Average width.*—Approximately 40 through 44 mm.

Form:
- *Shape.*—Generally — obolanceolate.
- *Marginal form.*—Doubly serrate.

*Color:*
- *Upper surface.*—Dark green, Plate 23, L-8, Page. 69; (125 M. O1 G).
- *Lower surface.*—Plate 23, H-6.

Glandular characteristics:
- *Numbers.*—Generally — one, occasionally two glands may be found.
- *Form.*—Reniform.

Petiole:
- *Length.*—Approximately 12 through 20 mm.
- *Thickness.*—Approximately 2 mm.

Stem glands: No stem glands are present.

Stipules: No stipules are evident.

Flower buds:
- *Size.*—Diameter — approximately 4 through 5 mm.
- *Form.*—Generally — conic and plump.
- *Surface texture.*—Glabrous.
- *Color.*—The color of the flower buds is not particularly distinctive.

Flowers:
- *Date of bloom.*—Approximately February 26 in the San Joaquin Valley of Central California.
- *Size.*—Generally — small, approximately 12 through 15 mm. in diameter when fully open.
- *Color.*—White, the color is not particularly distinctive of the subject variety.
- *Pistils.*—Numbers — one.
- *Stamens.*—Numbers — variable, approximately 28 through 30.

FRUIT

Maturity when described: Mature for harvesting and shipment approximately October 15 through October 20 at Orosi, Calif.

Size:
- *Generally.*—Medium.
- *Uniformity.*—Uniform.
- *Diameter in the Suture Plane.*—Variable, approximately 56 through 59 mm.
- *Diameter Transverse in the Suture Plane.*—Approximately 54 through 56 mm.
- *Diameter Transverse at Right Angles to the Suture Plane.*—Approximately 46 through 50 mm.

Form:
- *Uniformity.*—Uniform.
- *Symmetry.*—Symmetrical and round.
- *Suture.*—Prominent and distinct. Length — Approximately 80 mm. Position — Slightly depressed.

Stem cavity:
- *Depth.*—Approximately 12 mm.
- *Length.*—Approximately 18 mm.
- *Width.*—Approximately 12 mm.

Base:
- *Shape.*—Relatively flat with gently rounded sides.

Apex:
- *Shape.*—Somewhat rounded, and some slight protrusions are evident.

Pistil point: Not evident.

Stem:
- *Length.*—Approximately 17 mm.
- *Thickness.*—Approximately 2 mm.

Skin:
- *Thickness.*—Thin.
- *Texture.*—Average.
- *Tendency to crack.*—Slight.
- *Color.*—Plate 48, L-12, Page 119 (230. blackish P.).
- *Pubescence.*—Slight.

Flesh:
- *Color.*—Orange Brown, Plate 12, L-12, Page 47.
- *Surface texture of pit cavity.*—Smooth.
- *Color — Pit well.*—Plate 12, L-12, Page 47.
- *Amygdalin.*—Slight.
- *Juice production.*—Juicy.
- *Flavor.*—Sweet and subacid.
- *Aroma.*—Pleasing.
- *Texture.*—Fine grained.
- *Fibers.*—Generally — few, fine, and tender.
- *Ripening.*—Generally — even.
- *Eating quality.*—Good.

Stone:
- *Freestone or clingstone.*—Freestone.
- *Fibers.*—Not evident.
- *Length.*—Transverse in the suture plane — Approximately 19 through 20 mm.
- *Thickness.*—Approximately 8 through 9 mm.
- *Form.*—Generally — oval.
- *Base.*—Shape — flat with a pointed apex.
- *Sides.*—Form — three small grooves appear on the sides and are located near the base.

*Ridges.*—Generally — small ridges appear near the apex.

*Color.*—Plate 13, E-11 Page 49 (54 brO, 57 I Br).

Use: Fresh market.

Keeping quality: Excellent.

Shipping quality: Good.

Resistance to disease: No particular susceptibilities were noted.

Although the new variety of plum tree possesses the described characteristics as a result of the growing conditions prevailing near Orosi, Calif., in the Central part of the San Joaquin Valley, it is to be understood that variations of the usual magnitude and characteristics incident to growing conditions, fertilization, pruning and pest control are to be expected.

Having thus described and illustrated my new variety of plum tree, what is claimed as new and desired to be secured by Letters Patent is:

1. A new and distinct variety of Plum Tree, substantially as illustrated and described which is somewhat similar in its physical characteristics to the Angeleno Plum Tree (U.S. Plant Pat. No. 2,747) but from which is distinguished therefrom and characterized principally as to novelty by bearing fruit which are ripe for commercial harvesting and shipment from October 15 through October 20, the date of harvesting being approximately two or three weeks later than the Angeleno Plum Tree and which further bears fruit which have a substantially uniform shape and excellent storage and handling characteristics.

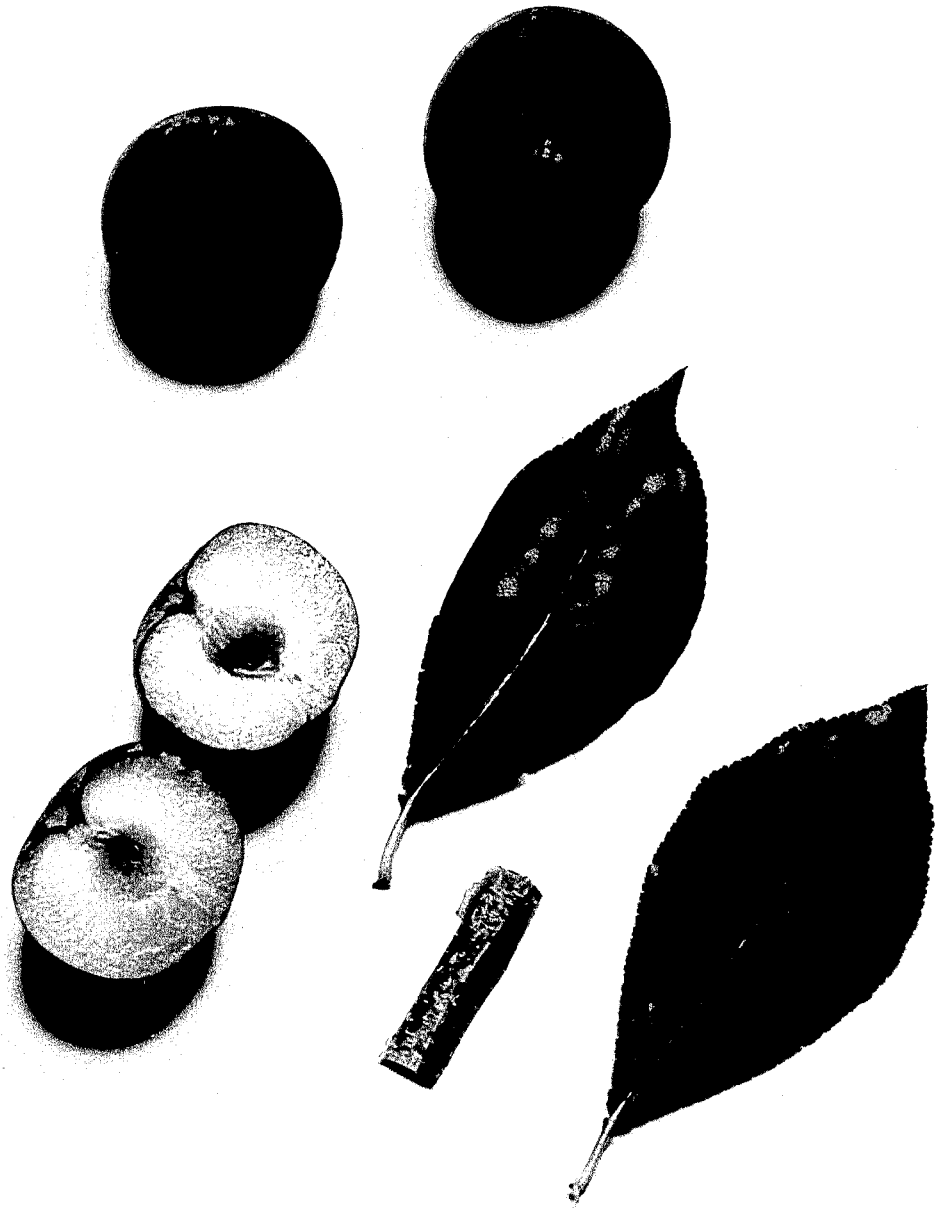

* * * * *